(12) United States Patent
Bühler et al.

(10) Patent No.: US 6,540,746 B1
(45) Date of Patent: Apr. 1, 2003

(54) BONE PLATE FOR SPLINTING A FRACTURE AT A BONE WITH A PLURALITY OF BONE SCREWS

(75) Inventors: Daniel W. Bühler, Wallisellen (CH); Hans K. Uhthoff, Ottawa (CA); David S. Backman, Gloucester (CA)

(73) Assignee: Sulzer Orthopedics Ltd., Baar (CH)

( * ) Notice: Subject to any disclaimer, the term of this patent is extended or adjusted under 35 U.S.C. 154(b) by 114 days.

(21) Appl. No.: 09/642,076

(22) Filed: Aug. 18, 2000

(30) Foreign Application Priority Data

Sep. 30, 1999 (EP) .............................. 99810881

(51) Int. Cl.[7] .............................................. A61B 17/80
(52) U.S. Cl. .......................................... 606/60; 606/69
(58) Field of Search .............................. 606/60, 61, 69, 606/70, 71

(56) References Cited

U.S. PATENT DOCUMENTS

| | | | | |
|---|---|---|---|---|
| 4,338,926 A | * | 7/1982 | Kummer et al. | 606/70 |
| 4,364,382 A | * | 12/1982 | Mennen | 606/69 |
| 4,943,292 A | | 7/1990 | Foux | 606/70 |
| 5,578,034 A | * | 11/1996 | Estes | 606/61 |
| 5,733,287 A | * | 3/1998 | Tepic et al. | 606/69 |
| 5,749,872 A | * | 5/1998 | Kyle et al. | 606/69 |

FOREIGN PATENT DOCUMENTS

| | | |
|---|---|---|
| EP | 0052998 A1 | 6/1982 |
| EP | 0266146 A2 | 5/1988 |
| GB | 2305483 A | 4/1997 |

* cited by examiner

Primary Examiner—Kevin Shaver
Assistant Examiner—Melba Bumgarner
(74) Attorney, Agent, or Firm—Townsend and Townsend and Crew LLP

(57) ABSTRACT

A bone plate for the splinting of a fracture at a bone with a plurality of bone screws. An elastic cushion is provided between the bone screws and the bone plate in the direction towards the fracture. The screw head penetrates through the bone plate completely and lies on the bone with a contact surface under a bias force. A ring body is molded onto the elastic cushion and can be mounted at the lower side of the bone plate. The ring body and the contact surface of the screw head both project beyond the lower side of the bone plate.

13 Claims, 2 Drawing Sheets

BONE PLATE FOR SPLINTING A FRACTURE AT A BONE WITH A PLURALITY OF BONE SCREWS

BACKGROUND OF THE INVENTION

The invention relates to a bone plate for the splinting of a fracture at a bone, comprising a plurality of bone screws which fix the bone plate to the bone with their screw head and which are radially braced in the direction towards the fracture via an elastic cushion of plastic to the bone plate in order to permit a restricted displacement in compression stressing of the bone.

In contrast to pressure plates, bone plates exert no compression during their application to the fracture of a bone. During securing with bone screws the bone parts remain unchanged in the longitudinal direction with respect to the bone plate.

A bone plate with elongated holes is shown in U.S. Pat. No. 4,943,292 (FOUX). A ring disc is provided between the securing head of a suitable bone screw and the bone plate and protrudes into an elongated hole with a projection in the form of a cushion on the side towards a provided bone fracture. An elastic plastic, which is also intended to enable sliding of the screw head when the cushion is pressed together in a compression of the bone, is provided as a material for the ring disc and the cushion. A problem in this arrangement is that the bone plate, which is pressed on the bone through the bone screw, should move relative to the bone. The tightening tension of the bone screw together with the friction between the plate and the bone determines the amount of a compression force, which leads to a displacement in the axial direction. Since the adhesive friction is practically always greater than the sliding friction, the displacement will take place in a jump-like manner as will moving back through the cushions when the compression force diminishes. A further disadvantage exists in that due to the large contact surfaces, large amounts of bone are disturbed in their blood circulation and decrease in their bone density (porosis).

SUMMARY OF THE INVENTION

The object of the invention is to improve these circumstances. The invention satisfies the object in that the screw head penetrates through the bone plate completely and lies on the bone with a contact surface which projects beyond the lower side of the bone plate by at least a distance $\epsilon_1$; and in that a ring body is formed at the cushion of plastic, can be applied with the cushion of plastic at the lower side of the bone plate and projects beyond the lower side by a distance $\epsilon_2$.

The invention has the advantage that, in contrast to pressure plates, which aim at a direct, callus-free primary healing, a secondary bone healing with controlled callus formation is enabled. Through the intentional distribution of the pressing force, which is active in the axial direction of the bone screw, onto a contact surface of the screw head which lies in contact at the bone and onto a ring body as an intermediate member, the frictional forces which counteract a longitudinal displacement of the bone plate are so small that the resilient action of the cushion of plastic actually comes to bear. In the fracture gap, which leads to the formation of a callus, the callus forming is stimulated through the intentionally permitted micro-movements in the longitudinal direction of the bone plate and, in the final analysis, a more rapid and solid healing is achieved.

The screw head is braced together with the bone independently of the frictional forces which counteract the longitudinal displacement of the bone plate, whereas the bias force on the bone plate, which is clamped between the screw head and the ring body, can be kept low. Since the bone plate itself is spaced apart from and hardly makes contact with the bone, no additional forces arise which influence the friction in the micro-movements.

Further improvements are achieved with additional optional features of the invention. Thus it is helpful to manufacture the ring body and the cushion of plastic in a single piece and to choose a compression modulus $E_c$ between 500 and 3,000 MPa for the elastic action. Through the choice of a bio-absorbable plastic for the cushion of plastic and the ring, a long-time action which is adapted to the healing process results. Because the bio-absorbable material slowly decomposes in the course of a plurality of weeks, the bone plate is clamped increasingly less severely in the course of time, and a continuously increasing stress is applied to the healing bone within the framework of narrow limits. Examples of such a material are polylactides. The Boehringer Company, Ingelheim, Germany, manufactures such a polylactide under the product designation Resomer R208, which decomposes in the human body through hydrolysis in approximately 30 weeks.

A further advantage lies in that large surface pressures are restricted to small, predetermined regions at the bone, with the proportion of pressure from the ring body steadily decreasing with the decomposition of the bio-absorbable material, so that the time point for the removal of the bone plate can be further delayed without great damage. The contact surface of the ring body and the screw head on the bone is more than 100% larger than the cross-section of the nominal diameter of the thread of the bone screw. It suffices to keep this contact surface smaller than eight times the cross-section of the nominal diameter of the thread in order to find within these limits (between 100% and 800%) a contact surface which is adapted to the thread of the bone screw with respect to the contact force which can be achieved.

Because the ring bodies can in each case be inserted in only one position into the bone plate and latch in this position, when they are connected to the ring body the cushions of plastic can be mounted only on the side of the fracture. For improved conformance to the rounding of tubular bones, the bone plate and the ring body can be concavely arched in the transverse direction at their lower side.

BRIEF DESCRIPTION OF THE DRAWINGS

The invention will be explained with reference to exemplary embodiments, in which.

DESCRIPTION OF THE PREFERRED EMBODIMENTS

Figure 1:
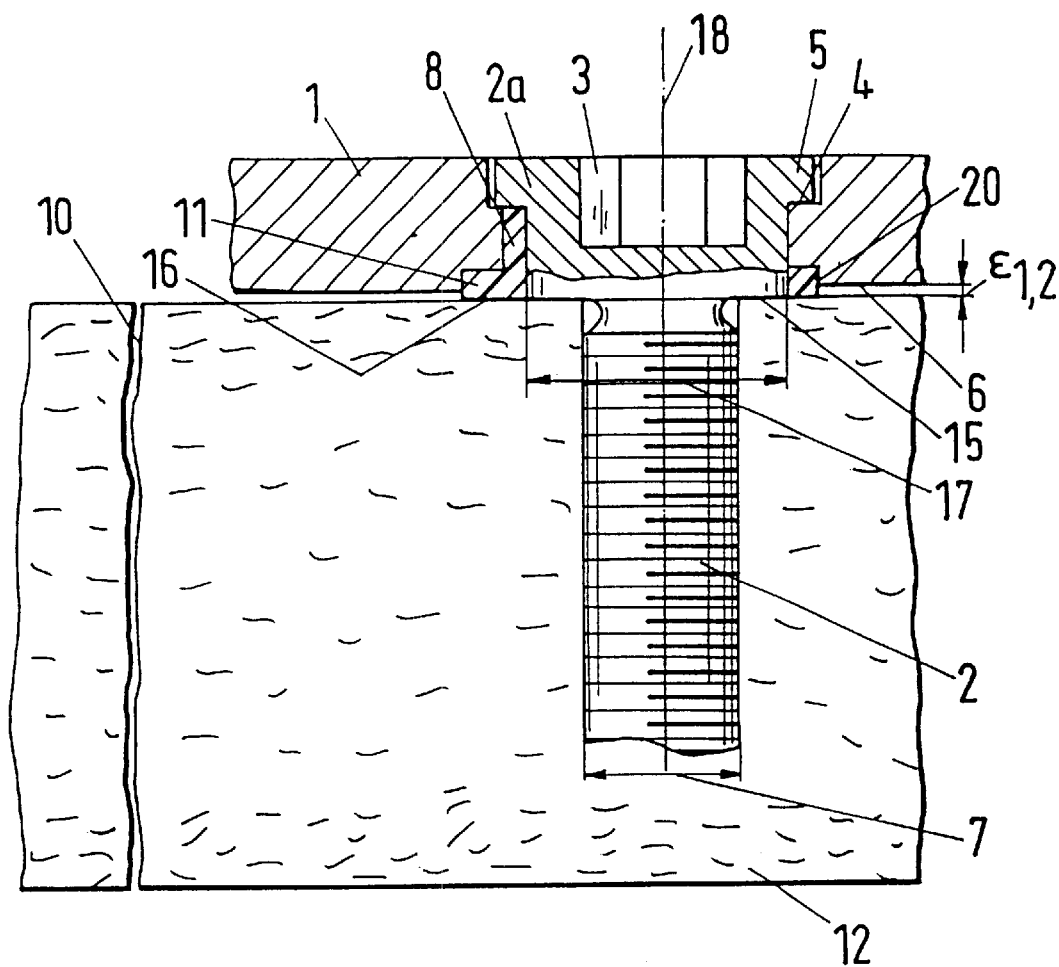
FIG. 1 illustrates schematically a section of a bone plate in accordance with the invention which is fixed with a bone screw in the vicinity of the fracture of a bone.

The figures show a bone plate for splinting a fracture 10 of a bone 12 with a plurality of bone screws 2. An elastic cushion of plastic 8 is provided between the bone screws 2 and the bone plate 1 in the direction towards the fracture 10. The screw head 2a penetrates completely through the bone plate 1 and lies with a contact surface 15 in contact on the bone under a bias force. A ring body 11 which can be mounted with the cushion of plastic 8 at the lower side 6 of the bone plate is molded onto the cushion of plastic 8. The ring body 11 and the contact surface 15 of the screw head 2a project beyond the lower side of the bone plate by distances $\epsilon_2$ and $\epsilon_1$, respectively, which need not be equally large.

Figure 5:
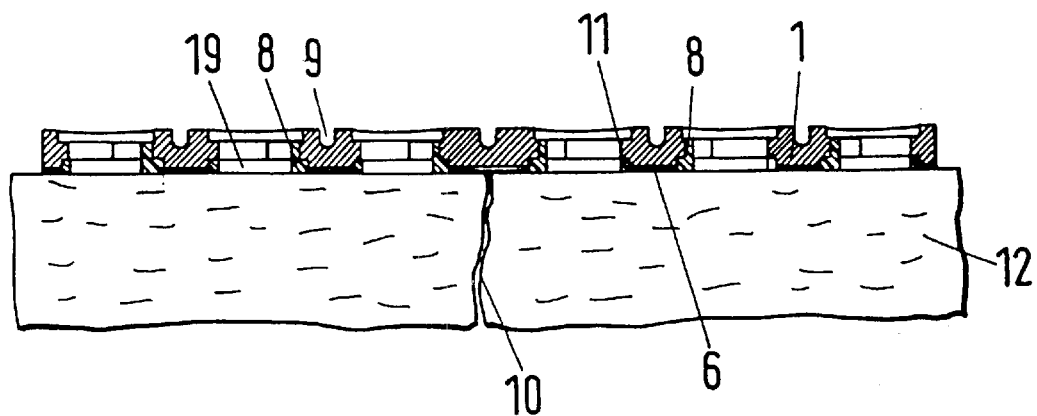
FIG. 5 illustrates schematically a longitudinal section through a bone plate with in each case three aligning elongated holes at both sides of the fracture of a bone.

An exemplary embodiment is shown in FIGS. 1 to 5. The same reference symbols are used in all figures. In FIG. 1 a bone screw 2 with its thread having a nominal diameter 7 of 3.5 mm is anchored in a bone 12 and is braced against the bone 12 with a contact surface 15 of its screw head 2a having a diameter 17 of 5.5 mm. Experiments have shown that the bone can sink in up to 200 $\mu$m below this contact surface 15. The screw head 2a, which is completely sunk in the bone plate 1 and which has an inner hexagon 3, has in its upper region a shoulder 5 which lies in contact with a ring-shaped ledge 4 in a bore 19 of the bone plate 1 and limits the plate's upward movement in the direction of the screw axis 18. On the lower side of the bone plate 1 a ring body 11 is pressed in and held by a snap connection 20. The contact surface 15 projects beyond lower side 6 of the bone plate by a distance $\epsilon_1$, which is at least so large that the lower side 6 does not lie in contact with the bone 12. The amount $\epsilon_1$ is chosen in each case to be greater than 0.2 mm in order that the lower side 6 of the bone plate reliably lies spaced apart from the bone between the bone screws 2. The ring body 11 likewise projects beyond the lower side 6 at its contact surface 16 by a distance $\epsilon_2$, which can be smaller than the distance $\epsilon_1$ for the screw contact surface 15, in order that the bone plate 1 is braced with only a limited force between the ring body 11 and the shoulder 5. A compression of the bone and a moving back is possible insofar as the elastic cushion of plastic 8, which is molded onto the ring body 11, and the friction between the shoulder 5 and the ledge 4, which is produced by the bias force, permit. In FIG. 5 three bores 19 which lie one behind the other are arranged at both sides of the fracture 10 with ring bodies 11, the cushions of plastic 8 of which are in each case arranged in the direction towards the fracture 10. The bores 19 are formed as elongated holes in order that the cushions 8 have room next to the circular screw head 2a which is to be inserted. Between the bores 19 and the lower side 6 of the bone plate 1 is a gap, and bone plate 1 has cut-outs 9 at the upper side which facilitate the adaptation to the bone shape in the longitudinal direction. Cut-outs for the reduction of the resistance torque are likewise possible on the sides of the bone plate between the bores. In the transverse direction the lower side 6 and the ring body 11 are concavely arched in order to conform to the bone shape in the transverse direction. Because the material for the cushion of plastic and the ring body is bio-absorbable, the deflections of the micro-movements can be controlled temporally in such a manner that during the backward movement of the surfaces of the cushion and the ring body, pressure peaks which become ever greater but still remain tractable are permitted at the fracture. The bone can thus take over its carrying function in accordance with the healing process, which has a very positive effect on bone forming.

A poly-D, L-lactide which is decomposed through hydrolysis in approximately 30 weeks is provided as a bio-absorbable plastic; for example the material Resomer R208 of the Boehringer Company, Ingelheim, Germany.

The material of the bone plate consists of titanium or of a titanium alloy such as Protasul™ of the applicant Sulzer Orthopedics Ltd.

Figure 2:
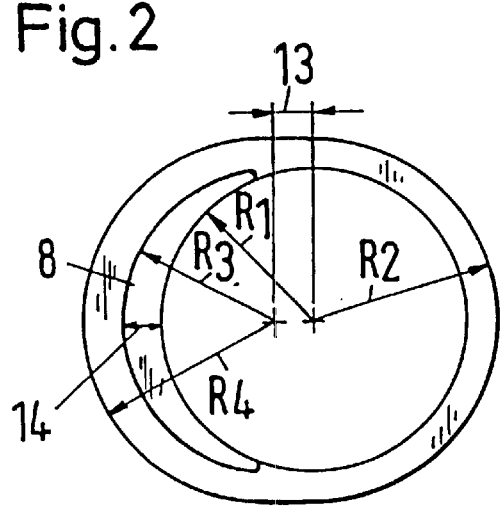
FIG. 2 illustrates schematically a plan view of a ring body with a sickle-shaped cushion of plastic.
Figure 3:
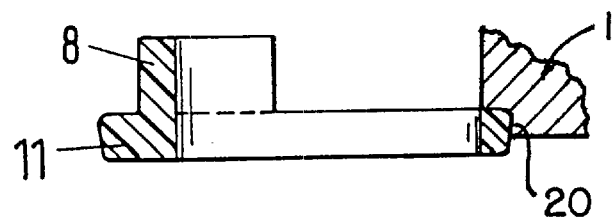
FIG. 3 illustrates schematically a cross-section through the ring body of FIG. 2.
Figure 4:
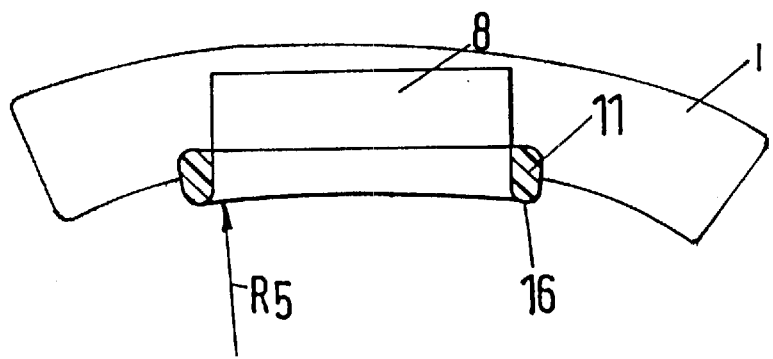
FIG. 4 illustrates schematically a longitudinal section through the ring body of FIG. 3.

For a bio-absorbable material of this kind FIGS. 2, 3 and 4 show a ring body 11 which is manufactured as an injection molded part onto which a sickle-shaped cushion 8 is molded. The injection molded part has a cylindrical inner surface with radius $R_1$ with which the screw head with its diameter 17 lies in contact. The outer contour of the sickle shape is bounded by a radius $R_3$ with the radius center displaced by a displacement 13 in the longitudinal direction. The outer contour of the actual ring body includes a radius $R_2$ with the same radius center as the radius $R_1$ and a radius $R_4$ with approximately the same radius center as the radius $R_3$, as well as the tangents at the circles $R_3$ and $R_4$. The sickle-shaped cushion 8 has a greatest thickness 14, which corresponds to 15% of the diameter 17 of the screw head 2a. This value can also be chosen smaller for a large compression modulus. The micro-movements are then smaller for the same compression force.

In FIG. 4 the contact surface 16 of the ring body 11 is concavely arched in the transverse direction with a curvature corresponding to a radius of curvature $R_5$.

What is claimed is:

1. A device for splinting a fracture of a bone, comprising:
   a bone plate having a bore therethrough and a lower surface adapted to be oriented toward a bone;
   a bone screw having a screw head adapted to extend through the bore of the bone plate so that a contact surface of the screw head projects beyond the lower surface of the bone plate by a first distance; and
   a ring body including an elastic cushion, the ring body being adapted to surround the screw head of the bone screw and to be inserted into the bore of the bone plate so that the elastic cushion is substantially inside the bore and oriented toward a fracture of a bone and so that a contact surface of the ring body projects beyond the lower surface of the bone plate by a second distance not larger than the first distance,
   wherein when the bone plate is attached to a bone by means of the bone screw, the contact surface of the screw head of the bone screw and the contact surface of the ring body contact an outer surface of the bone and hold the lower surface of the bone plate spaced apart from the bone, the elastic cushion allowing a restricted displacement of the bone and the bone screw relative to the bone plate.

2. The device in accordance with claim 1, wherein the material of the elastic cushion and of the ring body has a compression modulus between 500 and 3,000 MPa.

3. The device in accordance with claim 1, wherein the material of the elastic cushion and of the ring body is a bio-absorbable material which decomposes over a plurality of weeks.

4. The device in accordance with claim 3, wherein the bio-absorbable material is a polylactide which decomposes over approximately 30 weeks.

5. The device in accordance with claim 1, wherein the elastic cushion has a sickle shape.

6. The device in accordance with claim 5, wherein the sickle shape has a maximum sickle thickness in the direction toward the fracture; and the maximum sickle thickness corresponds to at least 8% of the diameter of the screw head.

7. The device in accordance with claim 1, wherein an area of the combined contact surfaces of the screw head and of the ring body which projects beyond the lower surface is more than 100% larger than a circular area defined by a nominal diameter of a thread of the bone screw.

8. The device in accordance with claim 1, wherein the ring body can be inserted in only one position in the bore of the bone plate and has a snap connection to the bone plate.

9. The device in accordance with claim 1, wherein the lower surface of the bone plate and the contact surface of the ring body are concavely arched in the transverse direction.

10. The device in accordance with claim 1, wherein the screw head of the bone screw is completely sunk in the bone plate.

11. The device in accordance with claim 1, wherein the bone plate further has a plurality of bores and a dimension of the bone plate is reduced by a cut out in a region between the bores in order to reduce bending stiffness in the region.

12. The device in accordance with claim 1, wherein the bone plate consists of titanium or a titanium alloy.

13. The device of claim 1, wherein the elastic cushion is made of a plastic material.

* * * * *